United States Patent [19]

Persidsky

[11] 4,269,718

[45] May 26, 1981

[54] PROCESS AND DEVICE FOR CENTRIFUGAL SEPARATION OF PLATELETS

[75] Inventor: Maxim D. Persidsky, San Francisco, Calif.

[73] Assignee: The Institutes of Medical Sciences, San Francisco, Calif.

[21] Appl. No.: 146,461

[22] Filed: May 5, 1980

[51] Int. Cl.³ .............................................. B01D 21/26
[52] U.S. Cl. .................................. 210/787; 210/927; 210/516; 233/26; 128/214 D
[58] Field of Search ................. 210/516, DIG. 23, 83, 210/78, 359, DIG. 24; 233/26; 128/214 D

[56] References Cited

U.S. PATENT DOCUMENTS

| | | | |
|---|---|---|---|
| 3,800,947 | 4/1974 | Smith | 210/DIG. 23 |
| 3,830,425 | 8/1974 | Stallmann | 233/26 |
| 3,960,727 | 6/1976 | Hochstrasser | 210/78 |
| 3,986,506 | 10/1976 | Garber et al. | 128/214 D |
| 4,007,871 | 2/1977 | Jones et al. | 210/DIG. 23 |
| 4,057,499 | 11/1977 | Buono | 210/516 |
| 4,213,561 | 7/1980 | Bayham | 233/26 |

OTHER PUBLICATIONS

Persidsky et al.; "Separation of Platelets by Modified Centrifugal Elutriation System"; *Blood*, vol. 52, #5, Supp. 1, p. 170; Nov. 1978.
Persidsky et al.; "Separation of Platelets by Centrifugal Elutriation"; *Cryobiology*, vol. 14, p. 700, (1977).

*Primary Examiner*—Benoit Castel
*Attorney, Agent, or Firm*—Limbach, Limbach & Sutton

[57] ABSTRACT

This invention relates to a method and apparatus for the separation of finely divided solid particles dissimilar in size and/or density, such as platelets and other blood cells. The separation of, for instance, platelets is accomplished by subjecting the blood sample to centrifugal force in the chamber while displacing the platelets from the blood sample by injecting a relatively small volume of saline into the centrifugally outer end of the chamber. In the preferred apparatus, the saline is injected into the blood sample by driving the chamber supporting the blood sample into a saline filled cavity under the influence of centrifugal force.

12 Claims, 4 Drawing Figures

PROCESS AND DEVICE FOR CENTRIFUGAL SEPARATION OF PLATELETS

The invention described herein was made in the course of work under a grant or award from the Department of Health, Education, and Welfare.

BACKGROUND OF INVENTION

Transfusion of platelets is now a widely used form of therapy for the treatment of hemorrhage in thrombocytopenic and thrombocytopathic patients. It is indispensable in the protocol treatment programs for acute leukemia, aplastic anemia, platelet deficiency, as well as replacement therapy in major surgical procedures.

Platelets are separated from whole blood as platelet-rich plasma (PRP) by procedures involving centrifugation. Transfusion of platelets is accomplished most often in a form of platelet-concentrates (PC) which are prepared by the high speed centrifugation of PRP. Several units of blood are required to obtain a sufficient number of platelets for therapeutic effectiveness. The use of multiple donors increases risks of isoimmunization and transmission of disease. In order to procure enough platelets from a single donor, the technique of plasmapheresis is required in which platelet-poor plasma (PPP) and packed red blood cells (RBC) are returned to the donor's blood circulation. The commonly used procedure of slow speed centrifugation with the routine equipment found in any blood bank is cumbersome, very time-consuming, and yields platelets heavily contaminated with white blood cells (WBC) and RBCs and gave low patelet recovery. A considerable improvement in the procurement of platelets has been made by the use of specialized blood processing equipment, Haemonetics-30, which permits the collection of two to four units of PC from a single donor. In this procedure, known as plateletpheresis, blood is pumped directly from the donor through a rotary seal into a centrifuge plastic bowl. Blood components are separated by forming concentric bands which overflow from the bowl in a sequence, depending on their specific density. This technique, however, permits one to harvest on the average only 46 percent of platelets from the blood circulating in the bowl. In order to collect the $4 \times 10^{11}$ platelets required for therapeutically effective transmission, at least 6 liters of blood must be processed, which takes from 2 to 3 hours of the donor's time. The operation is time-consuming and costly. Also, large initial investment for purchasing expensive equipment is required. Collected with this technique, platelets are heavily contaminated with WBCs and RBCs. Administration of PC contaminated with WBC may cause serious complications in patients. Platelets and WBC share HL-A antigens which are more immunogenic on WBC than those on platelets. As a result, WBC contamination may be responsible for the alloimmunization in patients which, in turn, causes with each consecutive transfusion progressive reduction in hemostatic effectiveness of platelets and, in more severe cases, may lead to post-transfusion thrombocytopenia. There are also systemic reactions which may occur within 20 minutes after completion of a platelet transfusion consisting of chills and fever. Antibodies to contaminating leucocytes are implicated in these reactions. Because of these side effects, removal of contaminating WBCs from PC by differential centrifugation is strongly recommended, which further complicates the procedure. Clearly, there is a need for improvement of platelet collection technique by making it safer and more effective in collecting PC at a higher yield, free of WBC and involving shorter time and lower cost than the present techniques offered.

SUMMARY OF INVENTION

My invention pertains broadly to centrifugal separation of finely divided solid particles. More particularly, the invention relates to a new process and a device for centrifugal separation of solid particles dissimilar in size and/or density, such as platelets and other blood cells or various types of synthetic particles and beads.

The art of separating finely divided dissimilar solid particles is largely based on differential sedimentation by centrifugation. The main problems inherent in this process are partial trapping of small particles by large ones and a lack of a sharp end point of separation during sedimentation. This confronts the users with a compromising situation where in order to increase the yield of separated particles, their purity will decrease and vice versa.

Bearing the above in mind, it is an object of the present invention to provide a new process and a device for the separation of finely divided solid particles dissimilar in size and/or density while allowing both maximum yield and purity of the separated particles. In order to accomplish this object, the existing process and system known as counterflow centrifugation (CC) or centrifugal elutriation (CE) have been substantially modified to adapt both of them for this new use.

In the CE process and system, developed by Beckman Company, the separation of particles is accomplished in a separation chamber within the Elutriator rotor. The tendency of particles to sediment in a centrifugal field is balanced in the chamber by a liquid flow in the opposite direction. By increasing the flow rate, smaller particles are washed out while larger or denser particles remain in the chamber. To accomplish the separation of particles, a large volume of liquid is made to pass through the separation chamber at a relatively high flow rate. Pumping of liquid into the rotor and through the separation chamber is accomplished by means of a rotary seal. Although both the Beckman system and their procedure are being successfully used for the separation of such blood cells as granulocytes, monocytes and young red cells, both of them are not suitable for the separation of platelets.

The object of this invention is to provide both a new design of the separation chamber effective for separation of widely dissimilar particles such as platelets and other blood cells and a new procedure for the accomplishment of the above goal. Based on may experimental study of chambers with different configurations, the one with a conical shape and larger in volume than the Beckman chamber, being 10.5 ml instead of 4.5 ml, was found to be most suitable for platelet separation. The reasons for this are that the conical chamber with about a 40° angle at its taper provides a steep and uniform fluid velocity gradient, directed against the centrifugal force gradient, thereby allowing one to keep blood cells in the chamber at a steady state equilibrium as a dense cell suspension with a sharp upper boundary which bears physical characteristics of a fluidized bed of particles. This fluidized bed of blood cells acts as a depth filter allowing platelets to pass through freely while retaining all other blood cells in the chamber. An important difference in this procedure from that of Beckman is that a very low flow rate of 3.5 ml/min and a small volume of medium of 5 to 8 ml are required for the separation of platelets, while for the separation of other blood cells by Beckman's CE procedure, flow rates from 15 to 25 ml/min and volumes of medium from 700 to 1000 ml are required. Also, separation of platelets by this process requires about two minutes for its completion, while the separation of other blood cells requires from 40 to 60 minutes. As a result, the separation process in the present invention can be characterized as a displacement process combined with the filtration in which a small volume of saline rapidly displaces PRP from whole blood. In contrast, cell separation by the CE process involves velocity sedimentation by washing with large volumes of medium. The supporting experimental evidence for the existence of the filtration action in such a fluidized bed of blood cells contained in the separation chamber is provided by unsuccessful attempts to remove the RBCs and WBCs contaminations from the PRP preparations collected by the Haemonetics-30 blood processor. Apparently, presence of a much lower number of blood cells in this PRP preparation, as compared to that with whole blood, did not permit attainment of the self-stabilizing and filtering action by the fluidized bed of blood cells, which resulted in the displacement of a large number of RBCs and WBCs together with PRP.

More particularly, it is an object to provide a new method for effective separation of PRP from whole blood, by preloading the separation chamber with blood outside the rotor rather than loading the chamber during centrifugation as in Beckman's procedure. Beckman's procedure for the loading of blood was found totally inadequate for the separation of platelets because it frequently caused packing of blood cells, resulting in blood hemolysis. By preloading the chamber with blood this problem is completely eliminated.

A further object in this new procedure is to allow initial clearance at the top of the chamber from blood cells by centrifugation for one minute without starting the counterflow of saline. This prevents an immediate elution of blood cells from the top of the chamber which would otherwise contaminate the exit line and prevent the collection of pure PRP.

Another object of this invention is to provide a self-contained system for the separation of dissimilar solid particles without involving the use of the Beckman Elutriator rotor. This is accomplished by replacing the Beckman external pumping system by an internal one using a piston pump incorporated into the unit containing the chamber. This unit is used as an insert in an centrifuge with swinging buckets. The pump in the unit is energized by centrifugal force and provides the necessary fluid flow within the separation chamber directed against centrifugal force. The flow rate is controlled by a needle valve.

DETAILED DESCRIPTION

Referring now to the accompanying drawings.

Figure 1:
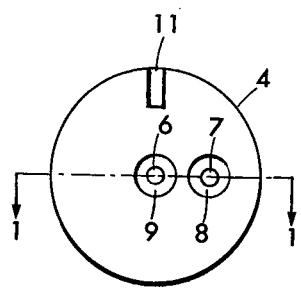
FIG. 1 is the upper plan view of the separation chamber.
Figure 2:
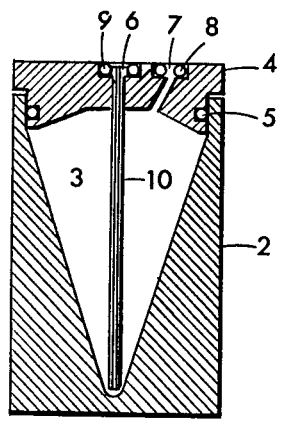
FIG. 2 is a vertical section of the separation chamber taken along the line 1—1 in FIG. 1.

The device shown in FIGS. 1 and 2 represents the separation chamber made to operate in the Beckman JE-6 Elutriator rotor and the Beckman J-21 preparative centrifuge. The main body of the chamber 2 has a conical cavity 3 and a lid 4 sealed with the o-ring 5. The lid has two ports, the central one 6 is the inlet port and the off-center one 7 is the outlet port. Both ports are sealed with the o-rings 8 and 9. Through the central port 6 a tube 10 is inserted which opens at a close proximity from the bottom of the chamber 3. The lid has a notch 11 which serves to locate the proper position of the chamber in the Beckman Elutriator rotor.

The separation chamber shown in FIGS. 1 and 2 represents an optimal design for the separation of platelets from whole blood. This design has been arrived at after an extensive experimental testing of many chambers of different geometrical shapes, including several conical ones with different angles at their taper, parabolic chambers with and without flare at their broad end, as well as the Beckman chamber. The latter one was found completely ineffective for the separation of platelets. The centrifugal elutriation procedure developed by the Beckman Company for the separation of different cells and particles was also found unsuitable for the above purpose.

My new procedure for the separation of platelets, or more specifically of platelet-rich plasma (PRP), from whole blood is as follows: A new separation chamber (FIGS. 1 and 2) is inserted into the Elutriator rotor and the Beckman system is primed with saline and purged of air. The rotor is then set on one side, without disconnecting its rotary seal from the external flow system, and the chamber is carefully removed without letting the air into the flow system. The chamber is then emptied of saline and filled with AC anticoagulated whole human blood. The inlet and outlet ports are covered with a strip of sheet plastic which was prior to that smeared with silicone grease. The chamber is then inserted into the Elutriator rotor and the plastic strip pulled out. Covering the chamber's ports with the plastic strip prevents both spillage of blood and the entrance of air into the system. The centrifuge is set at 2,500 rpm and after one minute from the start of centrifugation elutriation at a low flow rate of 3.5 ml/min is initiated. It is necessary to hold the elutriation flow for one minute to clear the top of the separation chamber by partial sedimentation of red blood cells (RBCs) and white blood cells (WBCs) in order to prevent contamination of PRP. After two minutes of centrifugation, collection of platelets is started. The first 2 ml contains only platelet-poor plasma (PPP), while consecutively eluted 6 to 8 ml of PRP contains about 90% of the total platelets in blood.

Platelets collected by this procedure contain no WBCs and a very small number of RBCs. Functionally, platelets appear normal as based on their morphology, ability to aggregate, take up serotonin, and in their survival time in the blood circulation of animals. Their ability to secrete ATP during aggregation is on the average 32% higher than that of control platelets obtained by slow speed centrifugation, which suggests that they are even more functionally intact than the control platelets.

Figure 3:
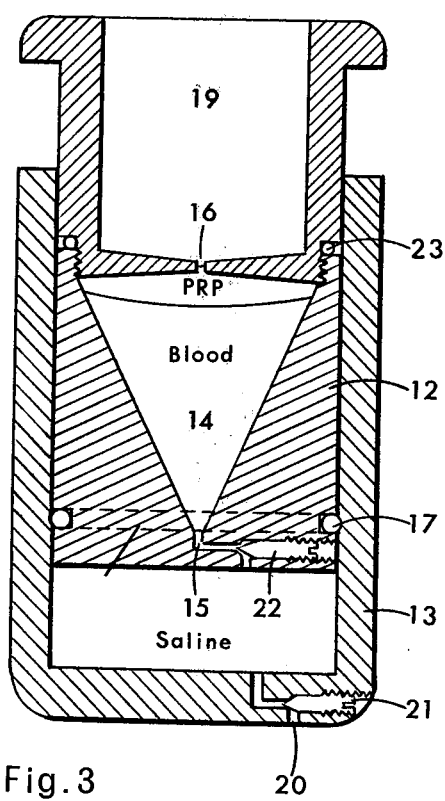
FIG. 3 is a vertical section of the apparatus taken along the vertical central axis and showing the plunger in the upper position.
Figure 4:
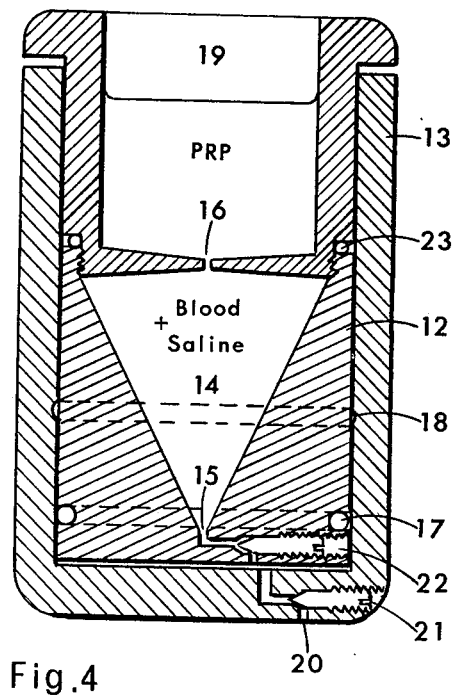
FIG. 4 is a vertical section of the apparatus taken along the vertical central axis and showing the plunger in the lower position.

The apparatus shown in FIGS. 3 and 4 represents a self-contained platelet separation system operating independently from the Beckman elutriator and used as an insert in any centrifuge with swinging buckets. The system incorporates a pump consisting of a piston 12 and a cylinder 13 which is operated by centrifugal force. Inside the piston 12 there is a conical chamber 14 with an inlet port 15 at its bottom and an outlet port 16 at its top. The o-ring 17 around the piston 12 provides the necessary seal with the cylinder 13. An annular groove 18 on the inner wall of the cylinder 13 serves to retain the o-ring 17 and to hold the plunger 12 in the upper position (FIG. 3) during the first minute of initial centrifugation at about 500 rpm. This provides the necessary delaying in the pumping action to allow partial sedimentation of blood in order to prevent contamination with blood of the upper collection chamber 19.

The platelet separation procedure using the device shown in FIGS. 3 and 4 starts by filling the lower part of the cylinder 13 with 15 ml of saline through the inlet port 20 and then closing the valve 21. The conical chamber 14 is then filled with 21 ml of AC anticoagulated whole blood. The device is then placed into the swinging bucket of the centrifuge and spun at about 500 rpm for one minute to clear the upper part of the chamber from the blood cells. Thereafter, the centrifuge speed is increased to about 2000 rpm. At this higher centrifugal force the o-ring 17 snaps off the groove 18 and the plunger 12 begins to descend, thereby initiating pumping action. The flow rate is preadjusted with the needle valve 22 to about 5 ml/min so that in about 3 minutes all saline is pumped out from the cylinder (FIG. 4) into the separation chamber 14 and thereby displacing all PRP from blood into the upper collection chamber 19. For the purpose of cleaning the collection chamber 19, it has screw arrangement and an o-ring 23 sealing it to the conical chamber 14.

Platelets collected with the system shown in FIGS. 3 and 4 are even purer than those obtained by my previous procedure involving the use of elutriator rotor and the chamber shown in FIGS. 1 and 2. In analyzing under a microscope more than $10^6$ cells, not a single white or red blood cell has been found. This system also allows harvesting close to 90% of the total platelets in blood. Isolated by this system, platelets are just as functional as those isolated by the previous system (FIGS. 1 and 2).

What is claimed is:

1. Apparatus for separating solid particles such as platelets from a blood sample comprising
    (a) a body adapted to be subjected to centrifugal force and containing a cavity adapted to receive a volume of displacing liquid therein,
    (b) a piston mounted in the body for movement into the cavity in response to centrifugal force on the piston with the piston containing a centrifugal chamber having inner and outer ends, and adapted to receive said sample from which particles are to be separated, and injection passageway means for movement of displacing liquid from the cavity to the centrifugal outer end of the chamber in response to movement of the piston into the cavity,
    (c) a discharge passageway at the centrifugally inner end of the chamber for discharging particle rich liquid in response to injection of displacing liquid into the chamber, and
    (d) means for preventing flow of displacing liquid from the cavity to the chamber before centrifugal stratification of blood cells in the chamber.

2. The apparatus of claim 1 characterized further by the inclusion of control means for preventing movement of the piston into the cavity until a minimum centrifugal force is applied to the piston.

3. The apparatus of claim 2 in which said control means comprises an O-ring on the piston received in a groove in the wall of the cavity.

4. The apparatus of claim 2 in which the control means comprises valve means activated by centrifugal force in said injection passageway means.

5. The apparatus of claim 1 characterized further by the inclusion of valve means in said injection passageway means for controlling the flow rate therein.

6. The apparatus of claim 1 characterized further by the inclusion of a blood sample in said chamber and a volume of buffered saline in the cavity.

7. The apparatus of claim 6 in which the body of saline has a volume between 0.2 and two times the volume of plasma in the blood sample.

8. The method of separating platelets from a blood sample comprising
    (a) supporting the blood sample in a centrifugal chamber having inner and outer ends,
    (b) subjecting the chamber to an intial centrifugal force of at least a predetermined minimum to stratify red cells in the sample away from the inner end, and
    (c) subjecting the chamber to a second centrifugal force while (1) injecting into the outer end of the chamber from a cavity, a displacing liquid having a volume of between 0.2 and two times the volume of plasma in the sample at a flow rate less than about 1.0 ml. per minute per ml. of the blood sample, and (2) displacing platelet rich plasma from the inner end of the chamber at substantially the same volume and rate with the displacing liquid ejected from the cavity by the second centrifugal force on the blood sample.

9. The method of claim 8 in which said chamber has a generally conical cross-section and said displacing liquid is buffered saline, and the chamber is subjected to a greater centrifugal force during the injection than during the stratification.

10. The method of claim 8 in which said displacing liquid is injected at a volume approximately equal to volume of plasma in the sample and at a rate of about 0.35 ml. per minute per ml. of the sample.

11. The method of claim 8 in which the step of injecting the displacing liquid into the chamber is performed by impounding the displacing liquid in a support cavity and propelling the blood sample containing chamber into the cavity under the influence of centrifugal force.

12. The method of claim 8 in which a sufficient number of blood cells are present in the chamber in order to form a dense cell suspension which has characteristics of a fluidized bed of particles and acts as a depth filter allowing platelets to pass through freely while maintaining other blood cells in a steady state equilibrium in the chamber.

* * * * *